(12) United States Patent
Helmer (10) Patent No.: US 11,730,879 B2
(45) Date of Patent: Aug. 22, 2023

(54) PACKAGING ASSEMBLY

(71) Applicant: SANOFI, Paris (FR)

(72) Inventor: Michael Helmer, Frankfurt am Main (DE)

(73) Assignee: Sanofi, Paris (FR)

( * ) Notice: Subject to any disclaimer, the term of this patent is extended or adjusted under 35 U.S.C. 154(b) by 287 days.

(21) Appl. No.: 16/958,084

(22) PCT Filed: Dec. 20, 2018

(86) PCT No.: PCT/EP2018/086098
§ 371 (c)(1),
(2) Date: Jun. 25, 2020

(87) PCT Pub. No.: WO2019/129617
PCT Pub. Date: Jul. 4, 2019

(65) Prior Publication Data
US 2021/0060234 A1    Mar. 4, 2021

(30) Foreign Application Priority Data

Dec. 28, 2017  (EP) ..................................... 17306949

(51) Int. Cl.
*A61M 5/00* (2006.01)
*G16H 20/17* (2018.01)
(Continued)

(52) U.S. Cl.
CPC .............. *A61M 5/002* (2013.01); *A61M 5/20* (2013.01); *F25D 11/00* (2013.01);
(Continued)

(58) Field of Classification Search
CPC ................... A61M 5/002; A61M 5/20; A61M 2205/3576; A61M 2205/3606;
(Continued)

(56) References Cited

U.S. PATENT DOCUMENTS

| 7,770,757 B2 | 8/2010 | Helmlinger |
| 2002/0017996 A1 | 2/2002 | Niemiec |

(Continued)

FOREIGN PATENT DOCUMENTS

| CN | 104955435 | 9/2015 |
| CN | 105102024 | 11/2015 |

(Continued)

OTHER PUBLICATIONS

PCT International Preliminary Report on Patentability in International Appln. No. PCT/EP2018/086098, dated Jun. 30, 2020, 7 pages.

(Continued)

*Primary Examiner* — Matthew Mikels
(74) *Attorney, Agent, or Firm* — Fish & Richardson P.C.

(57) ABSTRACT

A computing device comprises a memory and a data interface for connecting to a corresponding interface in a storage assembly. The memory comprises instructions which, on connection with the storage assembly, cause a processor of the storage assembly to: detect, using a device sensor of the storage assembly, one or more medicament delivery devices stored in the storage assembly; and display, on a display screen provided on the storage assembly, information relating to a medicament stored in the storage assembly.

20 Claims, 3 Drawing Sheets

(51) Int. Cl.
| | |
|---|---|
| *G16H 40/67* | (2018.01) |
| *G16H 40/20* | (2018.01) |
| *G16H 40/40* | (2018.01) |
| *H04W 76/10* | (2018.01) |
| *A61M 5/20* | (2006.01) |
| *F25D 11/00* | (2006.01) |
| *G06K 7/10* | (2006.01) |
| *G06K 7/14* | (2006.01) |
| *G06Q 10/0875* | (2023.01) |

(52) U.S. Cl.
CPC ..... *G06K 7/10297* (2013.01); *G06K 7/10861* (2013.01); *G06K 7/1413* (2013.01); *G06Q 10/0875* (2013.01); *G16H 20/17* (2018.01); *G16H 40/20* (2018.01); *G16H 40/40* (2018.01); *G16H 40/67* (2018.01); *H04W 76/10* (2018.02); *A61M 2205/3576* (2013.01); *A61M 2205/3606* (2013.01); *A61M 2205/502* (2013.01); *A61M 2205/52* (2013.01); *A61M 2205/6054* (2013.01); *A61M 2205/6063* (2013.01); *A61M 2205/6072* (2013.01); *G06K 2007/10504* (2013.01)

(58) Field of Classification Search
CPC ............. A61M 2205/502; F25D 11/00; G06K 7/10297; G06K 7/10861; G06K 7/1413; G06Q 10/0875; G16H 20/17; G16H 40/20; G16H 40/40; G16H 40/67; H04W 76/10
See application file for complete search history.

(56) References Cited

U.S. PATENT DOCUMENTS

| | | | |
|---|---|---|---|
| 2014/0155827 A1* | 6/2014 | Ostrander | A61J 7/0076 604/93.01 |
| 2017/0205138 A1 | 7/2017 | Hwang et al. | |

FOREIGN PATENT DOCUMENTS

| | | |
|---|---|---|
| CN | 107077451 | 8/2017 |
| EP | 1905469 | 4/2008 |
| JP | 2007-510469 | 4/2007 |
| JP | 2013-521963 | 6/2013 |
| JP | 2014-521424 | 8/2014 |
| WO | WO 2005/046559 | 5/2005 |
| WO | WO 2011/117212 | 9/2011 |
| WO | WO 2013/014219 | 1/2013 |
| WO | WO 2014/089083 | 6/2014 |
| WO | WO 2014/161955 | 10/2014 |
| WO | WO 2016/040512 | 3/2016 |
| WO | WO 2017/106247 | 6/2017 |

OTHER PUBLICATIONS

PCT International Search Report and Written Opinion in International Appln. No. PCT/EP2018/086098, dated Feb. 26, 2019, 9 pages.

* cited by examiner

PACKAGING ASSEMBLY

CROSS REFERENCE TO RELATED APPLICATIONS

The present application is the national stage entry of International Patent Application No. PCT/EP2018/086098, filed on Dec. 20, 2018, and claims priority to Application No. EP 17306949.3, filed on Dec. 28, 2017, the disclosures of which are incorporated herein by reference.

TECHNICAL FIELD

The application relates to a device for monitoring use of a medicament and, in particular, although not exclusively, to an electronic device configured to communicate with an external storage assembly.

BACKGROUND

Patients suffering chronic disease require regular treatment with medicaments, e.g. on the basis of a predefined schedule. Particular medicaments require refrigerated storage, and are often stored refrigerated in a household refrigerator or fridge. In a home treatment environment, the patient stores the medicament in their fridge and administers a predefined dose as required. The medicament may be provided in a pre-filled syringe or pen-type injector.

A medicament may have a predefined dosing schedule which requires the administration of a dose at relatively long intervals, for instance every two or four weeks, or once a month. The patient may be provided with several doses which may be stored in the fridge for 1 to 6 months for instance. It can be difficult for patients to keep track of each scheduled dosing time.

On the other hand, many household refrigerators may include 'smart' features such as, for example, a wired or wireless internet connection, Bluetooth connectivity, internet sensors and/or cameras for monitoring the contents of the fridge. A fridge can include a display providing a user interface to provide information to a user and receive instructions.

WO 2014/089083 relates to an electronic device for dispensing a medicament, and describes a magnetic stripe reader for reading e.g. prescription and/or patient information from a card.

US 2017/205138 relates to a refrigerator configured to interface with an external device e.g. a portable terminal device.

WO 2017/106247 describes a drug delivery system including a storage container and describes a controller coupled to the storage container, for example, the controller may be adapted to receive a sensed condition from a drug delivery device sensor of the storage container.

SUMMARY

In general, in one aspect, a computing device includes a memory and a data interface for connecting to a corresponding interface in a storage assembly. The memory includes instructions which, on connection with the storage assembly, cause a processor of the storage assembly to detect, using a device sensor of the storage assembly, one or more medicament delivery devices stored in the storage assembly, display, on a display screen provided on the storage assembly, information relating to a medicament stored in the storage assembly.

The device sensor of the storage assembly may include at least one of a camera, a radio-frequency sensor or a barcode scanner. The information relating to a medicament stored in the storage assembly may include one or more of a type of medicament, a dosage amount of the medicament, a dosage period for the medicament and an expiry date for the medicament. Instructions may further cause the processor of the storage assembly to provide the information relating to a medicament to one or more applications executed by the processor of the storage assembly, wherein the one or more applications are configured to display the information relating to a medicament on the display screen of the storage assembly.

The instructions may further cause the processor of the storage assembly to connect, through a wireless communication module of the storage assembly, to the internet, and transmit, through the wireless communication module, information relating to a medicament stored in the storage assembly. The transmission of information relating to a medicament may include, in response to detecting that a number of medicament delivery devices stored in the storage assembly is low, requesting one or more additional medicament delivery devices. The one or more medicament delivery devices may include one or more injection devices each including a medicament. The storage assembly may include a refrigerator appliance.

In general, in another aspect, a system includes a refrigerator appliance configured to store one or more medicament delivery devices, and further includes a computing device configured to provide the functions discussed above.

These and other aspects of the specification will be apparent from and elucidated with reference to the embodiments described hereinafter.

BRIEF DESCRIPTION OF THE FIGURES

Embodiments of the specification will now be described, by way of example only, with reference to the accompanying drawings, in which.

DETAILED DESCRIPTION

Embodiments of the specification provide a device configured to monitor the storage and use of a plurality of injection devices for delivering a medicament. An injection device is an example of a drug delivery device and may be a pen-injector or an auto-injector. The device is configured to establish communication with an external storage assembly. The device may be configured to provide an audio and/or visual reminder to a patient at a scheduled dosing time for the medicament, via the connected storage assembly. The storage assembly may further include one or more user interface elements for providing the patient with a status and information under the control of the connected device. The packaging assembly provides a predictable, easy to use operation for the patient.

The storage assembly may be a household refrigerator or fridge. The device may be configured to establish communication with the storage assembly through an interface.

A drug delivery device, as described herein, may be configured to inject a medicament into a patient. For example, delivery could be sub-cutaneous, intra-muscular, or intravenous. Such an injection device could be operated by a patient or care-giver, such as a nurse or physician, and can include various types of safety syringe, pen-injector, or auto-injector. The injection device can include a cartridge-based system that requires piercing a sealed ampule before use. Volumes of medicament delivered with these various injection devices can range from about 0.2 ml to about 3 ml. Yet another injection device can include a large volume device ("LVD") or patch pump, configured to adhere to a patient's skin for a period of time (e.g., about 5, 15, 30, 60, or 120 minutes) to deliver a "large" volume of medicament (typically about 2 ml to about 10 ml).

In combination with a specific medicament, the presently described injection devices may also be customized in order to operate within required specifications. For example, the device may be customized to inject a medicament within a certain time period (e.g., about 3 to about 20 seconds for auto-injectors, and about 10 minutes to about 60 minutes for an LVD). Other specifications can include a low or minimal level of discomfort, or to certain conditions related to human factors, shelf-life, expiry, biocompatibility, environmental considerations, etc. Such variations can arise due to various factors, such as, for example, a drug ranging in viscosity from about 3 cP to about 50 cP. Consequently, an injection device will often include a hollow needle ranging from about 25 to about 31 Gauge in size. Common sizes are 27 and 29 Gauge.

The injection devices described herein can also include one or more automated functions. For example, one or more of needle insertion, medicament injection, and needle retraction can be automated. Energy for one or more automation steps can be provided by one or more energy sources. Energy sources can include, for example, mechanical, pneumatic, chemical, or electrical energy. For example, mechanical energy sources can include springs, levers, elastomers, or other mechanical mechanisms to store or release energy. One or more energy sources can be combined into a single device. Devices can further include gears, valves, or other mechanisms to convert energy into movement of one or more components of a device.

The one or more automated functions of an auto-injector may be activated via an activation mechanism. Such an activation mechanism can include one or more of a button, a lever, a needle sleeve, or other activation component. Activation may be a one-step or multi-step process. That is, a user may need to activate one or more activation mechanism in order to cause the automated function. For example, a user may depress a needle sleeve against their body in order to cause injection of a medicament. In other devices, a user may be required to depress a button and retract a needle shield in order to cause injection.

In addition, such activation may activate one or more mechanisms. For example, an activation sequence may activate at least two of needle insertion, medicament injection, and needle retraction. Some devices may also require a specific sequence of steps to cause the one or more automated functions to occur. Other devices may operate with sequence independent steps.

Some delivery devices can include one or more functions of a safety syringe, pen-injector, or auto-injector. For example, a delivery device could include a mechanical energy source configured to automatically inject a medicament (as typically found in an auto-injector) and a dose setting mechanism (as typically found in a pen-injector).

Figure 1:
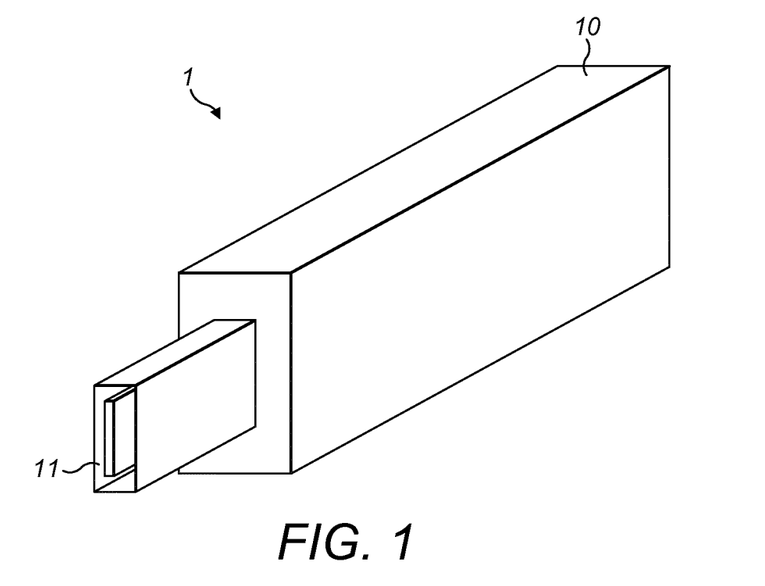
FIG. 1 is an isometric view of a device according to a first exemplary embodiment.

FIG. 1 shows an electronic device 1 according to a first embodiment. The electronic device 1 comprises a housing 10 and an interface 11. The housing 10 is generally rectangular in shape, and is elongate along a first axis. The interface 11 is located at a first end of the housing 10, referred to as a proximal end. The distal end of the housing is that furthest from the interface 11. The housing 10 is formed from plastic, and is formed from two substantially equal halves. Alternatively, the housing 10 may be formed from metal or from any other suitable material. The housing 10 is hollow, with an internal space forming an interior of the housing 10. The interface 11 is located at an exterior of the housing 10, although elements of the interface 11 pass through the housing 10 to the interior thereof.

The interface 11 comprises a data interface, which may be a serial data interface. The interface 11 is formed from metal and has the form of a plug, configured to interface with a corresponding socket. According to the embodiment, the interface 11 is formed as a male connector. Alternatively, the interface 11 may be formed as a female connector or socket, configured to interface with a corresponding plug. In some embodiments, the interface 11 may be formed from plastic or any other suitable material.

According to the embodiment, the interface 11 is a universal serial bus (USB) interface. The interface 11 is configured to transmit data to a connected corresponding interface, and to receive data therefrom. The interface 11 may be further configured to receive electrical power from a corresponding connected interface. In other embodiments, the interface 11 may be provided as any suitable data connection including, but not limited to, Firewire, Lightning, HDMI or eSATA.

Figure 2:
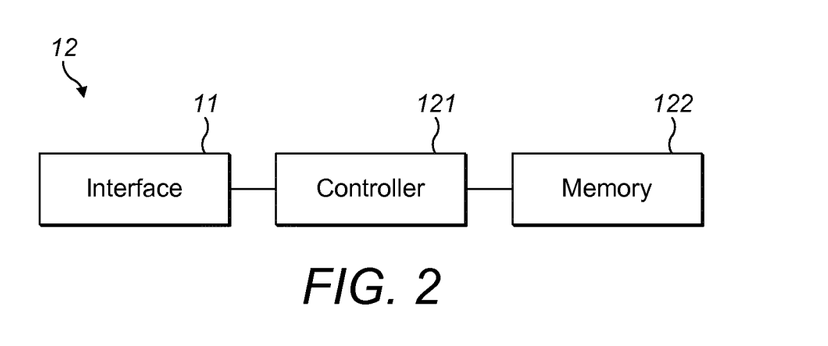
FIG. 2 is a block diagram of an electronics system of the device of FIG. 1, according to an exemplary embodiment.

The electronic device 1 includes an electronics system 12 (not visible in FIG. 1, but described with respect to in FIG. 2). The electronics system 12 comprises multiple components that are connected together to provide a specific set of functions, described below. The components of the electronics system 12 are mounted on a printed circuit board (PCB), although instead they may be interconnected through some other medium.

The electronics system 12 is configured to receive power through the interface when connected to a corresponding interface. Alternatively, the electronic device 1 may further comprise one or more battery cells. Further alternatively, the electronic device 1 may include a power supply input, comprising e.g. a socket for connection with a corresponding DC power adaptor. Any other form of power supply suitable for the electronics system 12 may be included.

The electronics system 12 is shown schematically in FIG. 2. The electronics system 12 comprises a controller 121 and a memory 122. The controller 121 is configured to control operation of the other hardware components of the electronics system 12. The controller 121 is further configured to control the operation of the interface 11. The memory 122 is configured to store instructions for the operation of the controller 121. The controller 121 may read and execute one or more instructions stored in the memory 122 in order to perform one or more operations or tasks. According to an operation, the controller 121 may control the interface 11 to transmit one or more data signals to a corresponding connected interface. The controller 121 may control the interface to transmit, for example, information or instructions to a corresponding connected interface.

Figure 3:
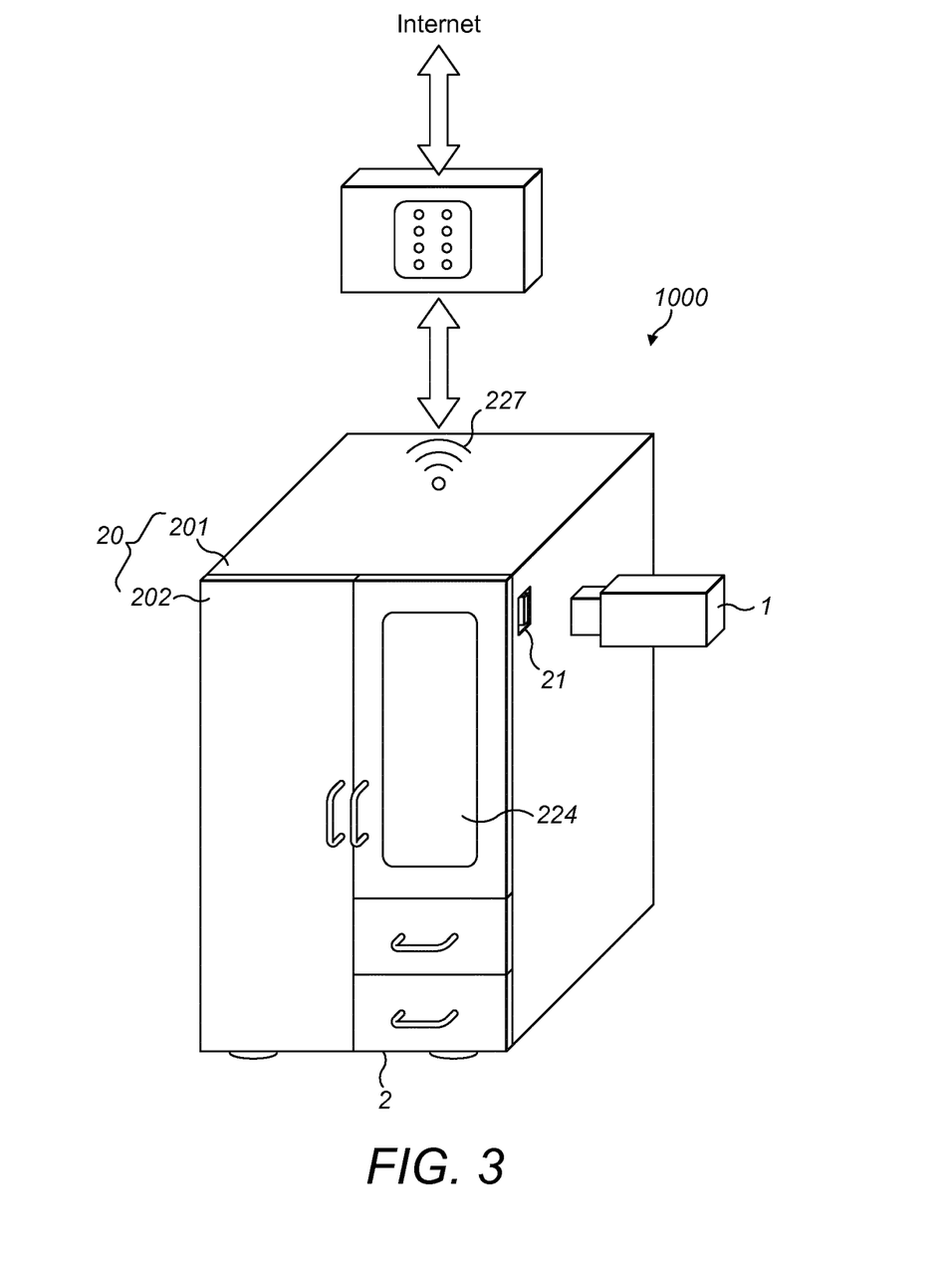
FIG. 3 is a system diagram of a system comprising the device of FIG. 1 in an exemplary operating environment.

FIG. 3 shows a system 1000 comprising the electronic device 1 and a refrigerator 2. The refrigerator 2 is an example of an external storage assembly. The refrigerator 2 is configured to store a plurality of injection devices 3. The refrigerator 2 comprises a housing 20, an interface 21, an electronics system 22 (shown in FIG. 4) and a power supply 23 (shown in FIG. 4).

The housing 20 is generally rectangular in shape. The housing 20 is generally formed from metal and plastic, and comprises a cabinet 201 and a door 202. The housing 20 is hollow, with an internal space forming an interior of the housing 20. The cabinet 201 is formed as an open box shape surrounding a hollow area, and the door 202 is configured to fit onto the cabinet 201 so as to enclose the hollow area. The interface 20 is located at an exterior of the housing 20, although elements of the interface 21 pass through the housing 20 to the interior thereof.

The door 202 of the refrigerator 2 is hinged so as to allow access to the interior by a user. In some embodiments the refrigerator 2 may be provided with more than one cabinet, for example, as a fridge in conjunction with a freezer, or may be provided with more than one door. The interior of the refrigerator 2 is provided with one or more shelves and or boxes to arrange goods within the refrigerator 2. The interior of the refrigerator 2 is cooled using electric power supplied by the power supply 23. The refrigerator 2 may be cooled to a temperature between 0 and 5 degrees C. Certain areas of the refrigerator 2, for example, one or more storage boxes provided within the refrigerator 2, may be cooled to a different temperature which is warmer or colder than the rest of the refrigerator 2.

Figure 4:
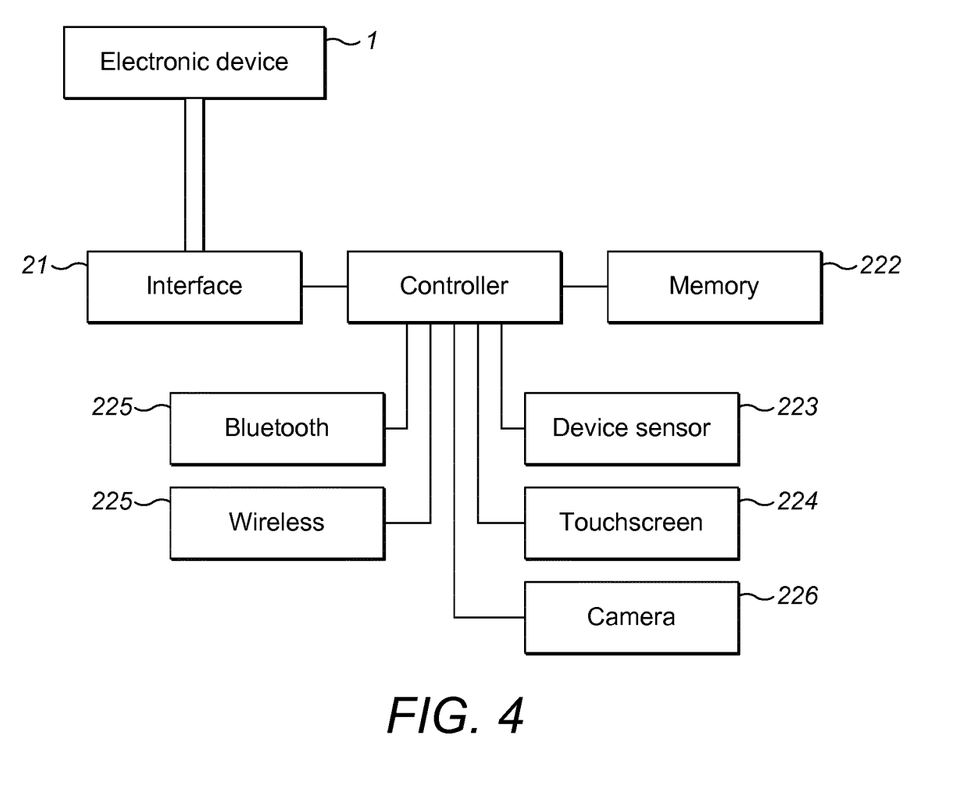
FIG. 4 is a block diagram of an electronics system for a device shown in FIG. 3.

The power supply 23 is supplied with mains power and provides electrical power for any motors or pumps required to cool the refrigerator 2. In addition, the power supply 23 provides electrical power to power the interface 21 and the elements of the electronic system.

The interface 21 comprises a data interface, which may be a serial data interface. The interface 21 is formed from metal and has the form of a socket, configured to interface with a corresponding plug. According to the embodiment, the interface 21 is formed as a female connector. Alternatively, the interface 21 may be formed as a male connector or plug, configured to interface with a corresponding socket. In some embodiments, the interface 21 may be formed from plastic or any other suitable material.

According to the embodiment, the interface 21 is a universal serial bus (USB) interface. The interface 21 is configured to transmit data to a connected corresponding interface, and to receive data therefrom. The interface 21 may be further configured to supply electrical power to a corresponding connected interface. The interface 21 may be configured to supply electrical power from the power supply 23 to a corresponding connected interface. In other embodiments, the interface 21 may be provided as any suitable data connection including, but not limited to, Firewire, Lightning, HDMI or eSATA.

The electronics system 22, as shown in FIG. 4, comprises multiple components that are connected together to provide a specific set of functions, described below. The components of the electronics system 22 are mounted on a printed circuit board (PCB), although instead they may be interconnected through some other medium. The electronics system 22 is configured to receive power from the power supply 23.

The electronics system 22 comprises a controller 221 and a memory 222. The controller 221 is configured to control operation of the other hardware components of the electronics system 22. The controller 221 is further configured to control the operation of the interface 21. The memory 222 is configured to store instructions for the operation of the controller 221. The controller 221 may read and execute one or more instructions stored in the memory 222 in order to perform one or more operations or tasks. The controller 221 may receive one or more data signals through the interface 21 from a corresponding connected interface. For example, the controller 221 may receive information or instructions through the interface 21 from a corresponding connected interface.

According to the embodiment, the electronics system 22 includes other hardware components of the refrigerator 2. The electronics system 22 comprises a device sensor 223, a touchscreen 224, a Bluetooth module 225, a camera 226 and a wireless connection module 227. Through the interface 21, the controller 221 may receive information or instructions sent by the electronic device 1 for controlling the hardware components of the electronic system 22.

The device sensor 223 is configured to detect one or more injection devices currently stored in the refrigerator 2. Alternatively, the device sensor 223 may be arranged to detect one or more injection device when they are placed into the refrigerator 2 or removed from the refrigerator 2. The device sensor 223 comprises at least one of a barcode reader, a radio-frequency identification (RFID) scanner or a mechanical sensor arranged to detect one or more injection devices by physical contact. Some or all operations of the device sensor 223 may alternatively be performed by the camera 226. In some embodiments, the device sensor 223 is arranged in a certain area of the refrigerator, for example, in a storage box configured to receive the one or more injection devices. Alternatively, the device sensor 223 may located in a convenient location for scanning each injection device as it is placed in or removed from the refrigerator. For example, the device scanner 223 may be placed on a front face of a storage box within the refrigerator 2 or on the door of the refrigerator.

The device scanner 223 may be provided with the refrigerator 2 for a purpose other than scanning injection devices. For example, the device scanner 223 may comprise a barcode reader provided for scanning one or more food items in the refrigerator. The electronic device 1 may send instructions causing one or more suitable hardware components of the electronics system 22 to operate as a device sensor 223.

The electronic device 1 may send instructions causing the device scanner 223 to perform a scanning operation and to provide a result of the scanning operation to the controller 221. For example, the electronic device 1 may transmit information for identifying one or more injection devices, with a request to perform a scanning operation based on the information. The electronic device 1 may transmit information for identifying the injection devices based on, for example, a barcode, RFID tag or an image or visual description of the injection devices. In some embodiments, the electronic device 1 may transmit a request for the refrigerator 2 to transmit sensor information identifying one or more suitable hardware components of the electronics system 22. The electronic device 1 may transmit information for identifying the injection devices based on the sensor information provided.

In some embodiments, the electronic device 1 may transmit first information for general identification of injection devices, for example, visual information based on the shape or colour of the injection devices. In response to receiving confirmation of detection of one or more injection devices, the electronic device 1 may transmit further information for specific identification of the injection devices, for example, visual information for identifying a type of medicament.

The instructions may further cause the controller 221 to transmit the result of the scanning operation through the interface 21 to the electronic device 1. The result of the scanning operation may comprise data indicating a number of injection devices, an identity of one or more of the injection devices and further information relating to one or more of the injection devices. Further information relating to one or more of the injection devices may include a type of medicament, a dosage amount of the medicament, a dosage period for the medicament and an expiry date for the medicament.

The touchscreen 224 may be arranged, for example, on a front face of the refrigerator 2 or internally within the refrigerator 2. Alternatively, the touchscreen 224 may be arranged in any position so as to be accessible to the user. In some embodiments, the touchscreen 224 may be remote from the refrigerator 2, for example, the touchscreen 224 may be connected to the electronics system 22 via the Bluetooth module 225 or the wireless connection module 227. In some embodiments, the electronics system 22 may connect with a mobile device of a user and operations described with respect to the touchscreen 224 may be performed by a touchscreen of the mobile device. The touchscreen 224 comprises a flat-panel display e.g. a LCD, OLED or an e-ink display. The touchscreen 224 further comprises a touch sensitive input e.g. a capacitive, resistive or infra-red touch sensor. In some embodiments, the electronics system 22 may include a display only, with an alternative form of user input, for example, a keyboard or number pad.

The electronic device 1 may send instructions causing the touchscreen 224 to display information relating to one or more injection devices. The information for display by the touchscreen 224 may be received from the electronic device 1 through the interface 21. The electronic device 1 may transmit information relating to the one or more injection device together with a request to display the information on the touchscreen 224. The electronic device 1 may transmit information based on a received result of the scanning operation. The information may be stored in the memory 122 and transmitted sent via the interface 11. In some embodiments, the information may be pre-stored in the memory 122 or may be received from the device scanner 223 and stored. Alternatively, the information may be provided by the controller 221. The information provided by the controller 221 may be received from the device scanner 223 or, alternatively, received from the Bluetooth module 225 or the wireless connection module 227.

The electronic device 1 may send instructions causing the touchscreen 224 to display a number of injection devices, an identity of one or more of the injection devices and further information relating to one or more of the injection devices. Further information relating to one or more of the injection devices may include a type of medicament, a dosage amount of the medicament, a dosage period for the medicament and an expiry date for the medicament.

The touchscreen 224 may be provided with the refrigerator 2 in order to display information other than information relating to the injections devices. For example, the touchscreen 224 may be provided to provide the user with information relating to food items in the refrigerator, or other useful information e.g. the news or the weather. The controller 221 may be configured to execute one or more applications, or 'apps', in conjunction with the touchscreen 224. For example, the controller 221 may execute a calendar application configured to display the user's calendar on the touchscreen 224 or a reminder application configured to display the user's to-do list or shopping list on the touchscreen.

In some embodiments, the electronic device 1 may request the controller 221 to transmit information relating to one or more applications executed by the controller 221. For example, the controller 221 may transmit information identifying one or more applications to the electronic device 1. The electronic device 1 may transmit instructions to the controller 221 for execution and operation of the one or more applications. For example, in an embodiment the electronic device 1 may transmit instructions causing the controller 221 to add an expiry date of an injection device to a user's calendar application, and to execute the calendar application such that the expiry date is displayed with the user's calendar on the touchscreen. The electronic device 1 may transmit instructions causing the controller 221 to add a scheduled injection time of an injection device to a user's reminder application, and to execute the reminder application such that the injection time is displayed with the user's to-do list on the touchscreen.

The Bluetooth module 225 may be provided in order for the electronics system 22 to communication with an external device, for example, a mobile device of a user. The Bluetooth module 225 may be configured to send information to a mobile device, e.g. to send an alert when the door 202 is open, or to receive information from the mobile device, e.g. to synchronise one or more user applications between the mobile device and the refrigerator 2.

The electronic device 1 may send instructions causing the Bluetooth module 225 to send information to the mobile device relating to one or more injection devices. The information for sending by the Bluetooth module 225 may be received from the electronic device 1 through the interface 21. The information may be stored in the memory 122 and transmitted sent via the interface 11. In some embodiments, the information may be pre-stored in the memory 122 or may be received from the device scanner 223 and stored. Alternatively, the information may be provided by the controller 221. The information provided by the controller 221 may be received from the device scanner 223 or, alternatively, received from the Bluetooth module 225 or the wireless connection module 227 from an external source other than the mobile device.

The electronic device 1 may send instructions causing the Bluetooth module 225 to send information including a number of injection devices, an identity of one or more of the injection devices and further information relating to one or more of the injection devices. Further information relating to one or more of the injection devices may include a type of medicament, a dosage amount of the medicament, a dosage period for the medicament and an expiry date for the medicament.

The electronic device 1 may send instructions causing the Bluetooth module 225 to communicate with one or mobile additional external devices. The electronic device 1 may provide connection information to configure a connection between the Bluetooth module 225 and one or more external devices, for example, one or more injection devices or an external device configured to monitor the one or more injection devices. The one or more injection devices or an external device monitoring the injection devices may be configured to measure and record e.g. a temperature of the injection devices and communicate measurements via Bluetooth to the Bluetooth interface 225. The electronic device 1 may send instructions causing the Bluetooth module 225 to provide received measurements to the controller 221 or to the electronic device 1.

The camera 226 may be provided to monitor the contents of the refrigerator 2 e.g. to monitor one or more food items stored in the refrigerator 2. The camera 226 may be arrange on an inside of the door 202 or, alternatively, may be arrange in a certain area of the refrigerator, for example, in a storage box configured to receive the one or more injection devices. The electronic device 1 may send instructions causing the camera 226 to record a number and/or type of injection devices stored in the refrigerator 2. In this way, the camera 226 may perform some or all of the operations of the device scanner 223. The electronic device 1 may send instructions causing the camera 226 to function as a barcode reader.

The wireless connection module 227 may be provided for the electronics system 22 to connect with a wireless local area network (wLAN). The wireless connection module 227 may provide the electronics system 22 with an internet connection through the wLAN. In some embodiments, the electronics system 22 may be connected to the internet through a wired connection e.g. through an ethernet connection. The electronics system 22 may receive information through the wireless connection module 227, for example, the wireless connection module 227 may receive weather information from the internet. The controller 221 may control the touchscreen 224 to display information received through the wireless connection module 227. The electronics system 22 may transmit information through the wireless connection module 227. For example, the controller 221, in response to detecting the removal of a food item from the refrigerator 2, may transmit an order for a replacement food item via the internet.

The electronic device 1 may send instructions causing the wireless connection module 227 to transmit a request for one or more injection devices through the internet. In response to determining that the number of injection devices stored in the refrigerator 2 is, for example, one or zero, the electronic device 1 may cause the wireless connection module 227 to transmit a request for replacement injection devices.

The terms "drug" or "medicament" are used synonymously herein and describe a pharmaceutical formulation containing one or more active pharmaceutical ingredients or pharmaceutically acceptable salts or solvates thereof, and optionally a pharmaceutically acceptable carrier. An active pharmaceutical ingredient ("API"), in the broadest terms, is a chemical structure that has a biological effect on humans or animals. In pharmacology, a drug or medicament is used in the treatment, cure, prevention, or diagnosis of disease or used to otherwise enhance physical or mental well-being. A drug or medicament may be used for a limited duration, or on a regular basis for chronic disorders.

As described below, a drug or medicament can include at least one API, or combinations thereof, in various types of formulations, for the treatment of one or more diseases. Examples of API may include small molecules having a molecular weight of 500 Da or less; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more drugs are also contemplated.

The term "drug delivery device" shall encompass any type of device or system configured to dispense a drug or medicament into a human or animal body. Without limitation, a drug delivery device may be an injection device (e.g., syringe, pen injector, auto injector, large-volume device, pump, perfusion system, or other device configured for intraocular, subcutaneous, intramuscular, or intravascular delivery), skin patch (e.g., osmotic, chemical, microneedle), inhaler (e.g., nasal or pulmonary). The presently described drugs may be particularly useful with injection devices that include a needle, e.g., a hypodermic needle for example having a Gauge number of 24 or higher.

The drug or medicament may be contained in a primary package or "drug container" adapted for use with a drug delivery device. The drug container may be, e.g., a cartridge, syringe, reservoir, or other solid or flexible vessel configured to provide a suitable chamber for storage (e.g., short- or long-term storage) of one or more drugs. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of the pharmaceutical formulation to-be-administered (e.g., an API and a diluent, or two different drugs) separately, one in each chamber. In such instances, the two chambers of the dual-chamber cartridge may be configured to allow mixing between the two or more components prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drugs or medicaments contained in the drug delivery devices as described herein can be used for the treatment and/or prophylaxis of many different types of medical disorders. Examples of disorders include, e.g., diabetes mellitus or complications associated with diabetes mellitus such as diabetic retinopathy, thromboembolism disorders such as deep vein or pulmonary thromboembolism. Further examples of disorders are acute coronary syndrome (ACS), angina, myocardial infarction, cancer, macular degeneration, inflammation, hay fever, atherosclerosis and/or rheumatoid arthritis. Examples of APIs and drugs are those as described in handbooks such as Rote Liste 2014, for example, without limitation, main groups 12 (anti-diabetic drugs) or 86 (oncology drugs), and Merck Index, 15th edition.

Examples of APIs for the treatment and/or prophylaxis of type 1 or type 2 diabetes mellitus or complications associated with type 1 or type 2 diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the terms "analogue" and "derivative" refers to any substance which is sufficiently structurally similar to the original substance so as to have substantially similar functionality or activity (e.g., therapeutic effectiveness). In particular, the term "analogue" refers to a polypeptide which has a molecular structure which formally can be derived from the structure of a naturally occurring peptide, for example that of human insulin, by deleting and/or exchanging at least one amino acid residue occurring in the naturally occurring peptide and/or by adding at least one amino acid residue. The added and/or exchanged amino acid residue can either be codable amino acid residues or other naturally occurring residues or purely synthetic amino acid residues. Insulin analogues are also referred to as "insulin receptor ligands". In particular, the term "derivative" refers to a polypeptide which has a molecular structure which formally can be derived from the structure of a naturally occurring peptide, for example that of human insulin, in which one or more organic substituent (e.g. a fatty acid) is bound to one or more of the amino acids. Optionally, one or more amino acids occurring in the naturally occurring peptide may have been deleted and/or replaced by other amino acids, including non-codeable amino acids, or amino acids, including non-codeable, have been added to the naturally occurring peptide.

Examples of insulin analogues are Gly(A21), Arg(B31), Arg(B32) human insulin (insulin glargine); Lys(B3), Glu (B29) human insulin (insulin glulisine); Lys(B28), Pro(B29) human insulin (insulin lispro); Asp(B28) human insulin (insulin aspart); human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Examples of insulin derivatives are, for example, B29-N-myristoyl-des(B30) human insulin, Lys(B29) (N-tetradecanoyl)-des(B30) human insulin (insulin detemir, Levemir®); B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-gamma-glutamyl)-des(B30) human insulin, B29-N-omega-carboxypentadecanoyl-gamma-L-glutamyl-des(B30) human insulin (insulin degludec, Tresiba®); B29-N—(N-lithocholyl-gamma-glutamyl)-des(B30) human insulin; B29-N-(ω-carboxyheptadecanoyl)-des(B30) human insulin and B29-N-(ω-carboxyhepta¬decanoyl) human insulin.

Examples of GLP-1, GLP-1 analogues and GLP-1 receptor agonists are, for example, Lixisenatide (Lyxumia®), Exenatide (Exendin-4, Byetta®, Bydureon®, a 39 amino acid peptide which is produced by the salivary glands of the Gila monster), Liraglutide (Victoza®), Semaglutide, Taspoglutide, Albiglutide (Syncria®), Dulaglutide (Trulicity®), rExendin-4, CJC-1134-PC, PB-1023, TTP-054, Langlenatide/HM-11260C, CM-3, GLP-1 Eligen, ORMD-0901, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, TT-401, BHM-034. MOD-6030, CAM-2036, DA-15864, ARI-2651, ARI-2255, Exenatide-XTEN and Glucagon-Xten.

An example of an oligonucleotide is, for example: mipomersen sodium (Kynamro®), a cholesterol-reducing antisense therapeutic for the treatment of familial hypercholesterolemia.

Examples of DPP4 inhibitors are Vildagliptin, Sitagliptin, Denagliptin, Saxagliptin, Berberine.

Examples of hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Examples of polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20 (Synvisc®), a sodium hyaluronate.

The term "antibody", as used herein, refers to an immunoglobulin molecule or an antigen-binding portion thereof. Examples of antigen-binding portions of immunoglobulin molecules include F(ab) and F(ab')2 fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region. The term antibody also includes an antigen-binding molecule based on tetravalent bispecific tandem immunoglobulins (TBTI) and/or a dual variable region antibody-like binding protein having cross-over binding region orientation (CODV).

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the present specification include, for example, Fab fragments, F(ab')2 fragments, scFv (single-chain Fv) fragments, linear antibodies, monospecific or multispecific antibody fragments such as bispecific, trispecific, tetraspecific and multispecific antibodies (e.g., diabodies, triabodies, tetrabodies), monovalent or multivalent antibody fragments such as bivalent, trivalent, tetravalent and multivalent antibodies, minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen. Examples of antibodies are anti PCSK-9 mAb (e.g., Alirocumab), anti IL-6 mAb (e.g., Sarilumab), and anti IL-4 mAb (e.g., Dupilumab).

Pharmaceutically acceptable salts of any API described herein are also contemplated for use in a drug or medicament in a drug delivery device. Pharmaceutically acceptable salts are for example acid addition salts and basic salts.

Those of skill in the art will understand that modifications (additions and/or removals) of various components of the APIs, formulations, apparatuses, methods, systems and embodiments described herein may be made without departing from the full scope and spirit of the present specification, which encompass such modifications and any and all equivalents thereof.

The invention claimed is:

1. A computing device comprising:
  a memory; and
  a data interface for connecting to a corresponding interface in a storage assembly,
  wherein the memory comprises instructions,
  wherein when the computing device is connected with the storage assembly, the computing device is configured to send the instructions to the storage assembly, the instructions causing a processor of the storage assembly to:
    detect, using a device sensor of the storage assembly, one or more medicament delivery devices stored in the storage assembly; and
    display, on a display screen provided on the storage assembly, information relating to a medicament stored in the storage assembly.

2. The computing device of claim 1, wherein the device sensor of the storage assembly comprises at least one of a camera, a radio-frequency sensor, or a barcode scanner.

3. The computing device of claim 1, wherein the information relating to the medicament stored in the storage assembly comprises information relating to one or more of a type of medicament, a dosage amount of the medicament, a dosage period for the medicament, or an expiry date for the medicament.

4. The computing device of claim 1, wherein the instructions further cause the processor of the storage assembly to provide the information relating to the medicament to one or more applications executed by the processor of the storage assembly, wherein the one or more applications are configured to display the information relating to the medicament on the display screen of the storage assembly.

5. The computing device of claim 1, wherein the instructions further cause the processor of the storage assembly to:
  connect, through a wireless communication module of the storage assembly, to the internet; and
  transmit, through the wireless communication module, the information relating to the medicament stored in the storage assembly.

6. The computing device of claim 5, wherein the transmission of the information relating to the medicament comprises, in response to detecting that a number of medicament delivery devices stored in the storage assembly is low, requesting one or more additional medicament delivery devices.

7. The computing device of claim 1, wherein the one or more medicament delivery devices comprise one or more injection devices each comprising the medicament.

8. The computing device of claim 1, wherein the storage assembly comprises a refrigerator appliance.

9. A system comprising:
  a storage assembly configured to store one or more medicament delivery devices, the storage assembly comprising a processor, an interface, a device sensor, and a display; and
  a computing device comprising
    a memory, and
    a data interface for connecting to the interface of the storage assembly,
  wherein the memory comprises instructions,
  wherein when the computing device is connected with the storage assembly, the computing device is configured to send the instructions to the storage assembly, the instructions causing the processor of the storage assembly to:
    detect, using the device sensor of the storage assembly, one or more medicament delivery devices stored in the storage assembly; and
    display, on the display screen provided on the storage assembly, information relating to a medicament stored in the storage assembly.

10. The system of claim 9, wherein the device sensor of the storage assembly comprises at least one of a camera, a radio-frequency sensor, or a barcode scanner.

11. The system of claim 9, wherein the information relating to the medicament stored in the storage assembly comprises one or more of a type of medicament, a dosage amount of the medicament, a dosage period for the medicament and an expiry date for the medicament.

12. The system of claim 9, wherein the instructions further cause the processor of the storage assembly to provide the information relating to the medicament to one or more applications executed by the processor of the storage assembly, wherein the one or more applications are configured to display the information relating to the medicament on the display screen of the storage assembly.

13. The system of claim 9, wherein the instructions further cause the processor of the storage assembly to:
  connect, through a wireless communication module of the storage assembly, to the internet; and
  transmit, through the wireless communication module, the information relating to the medicament stored in the storage assembly.

14. The system of claim 13, wherein the transmission of the information relating to the medicament comprises, in response to detecting that a number of medicament delivery devices stored in the storage assembly is low, requesting one or more additional medicament delivery devices.

15. The system of claim 9, wherein the one or more medicament delivery devices comprise one or more injection devices each comprising the medicament.

16. The system of claim 9, wherein the storage assembly comprises a refrigerator appliance.

17. A method comprising:
  detecting, using a device sensor of a storage assembly, one or more medicament delivery devices stored in the storage assembly; and
  displaying, on a display screen provided on the storage assembly, information relating to a medicament stored in the storage assembly.

18. The method of claim 17, wherein the storage assembly comprises a refrigerator appliance.

19. The method of claim 17, further comprising:
  causing the information relating to a medicament on the display screen of the storage assembly to be displayed.

20. The method of claim 17, further comprising:
  connecting, through a wireless communication module of the storage assembly, to the internet; and transmitting, through the wireless communication module, the information relating to the medicament stored in the storage assembly.

\* \* \* \* \*